United States Patent [19]

Steplewski et al.

[11] Patent Number: 5,169,775
[45] Date of Patent: Dec. 8, 1992

[54] MONOCLONAL ANTIBODIES AGAINST LYMPHOMA-ASSOCIATED ANTIGENS, HYBRID CELL LINES PRODUCING THESE ANTIBODIES

[75] Inventors: Zenon Steplewski, Malvern; K. Ann Jeglum, West Chester, both of Pa.

[73] Assignee: The Wistar Institute, Philadelphia, Pa.

[21] Appl. No.: 545,590

[22] Filed: Jun. 29, 1990

Related U.S. Application Data

[63] Continuation of Ser. No. 44,285, Apr. 3, 1987.

[51] Int. Cl.$^5$ .............. C12N 5/12; C07K 15/28; C12P 21/08
[52] U.S. Cl. .............. 435/240.27; 530/388.1; 530/387.3; 530/388.8
[58] Field of Search ........... 530/387, 388.1, 388.8, 530/387.3; 435/240.27; 424/85.8; 935/104, 110, 107, 108

[56] References Cited

U.S. PATENT DOCUMENTS 4,444,744  4/1984  Goldenberg .................. 424/1.1

OTHER PUBLICATIONS

Sun, L. K. et al., Hybridoma, 5(Suppl):517–520, 1986.
Sarmiento, U. M. et al., Can J Vet Res., 51:110–116, 1987.
Appelbaum, et al., "Phenotyping of Canine Lymphoma with Monoclonal Antibodies Directed at Cell Surface Antigens: Classification, Morphology, Clinical Presentation and Response to Chemotherapy," Hematological Oncology, vol. 2, 151–168 (1984).
Krawiec, et al., "Development and Characterization of a Hybridoma-Derived Antibody (Aby 1A1) With Specificity to Canine Thymocytes and Peripheral T Lymphocytes," Am. J. Vet. Res., vol. 45, No. 3, 491–498.
Wulff, et al., "A Monoclonal Antibody (DT-2) Recognizing Canine T Lymphocytes," Transplantation, vol. 33, No. 4, 616–620 (1982).
Deeg, et al., "Unusual Distribution of Ia-Like Antigens on Canine Lymphocytes," Immunogenetics, vol. 16, 445–457 (1982).
Ladiges, et al., "Monoclonal Antibodies to Canine Cell Surface Antigens: A Comparison of Screening Assays," Hybridoma, vol. 3, No. 4, 387–390 (1984).
McKenzie, et al., "Studies With a Monoclonal Antibody on the Distribution of Thy-1 in the Lymphoid and Extracellular Connective Tissues of the Dog," Transplantation, vol. 31, No. 4, 275–282 (1981).
Schuenig et al., "Failure of Autologous Marrow Reconstitution After Cytolytic Treatment with Anti-Ia Monoclonal Antibody," Exp. Hematology (1984), vol. 12, 423, Abstract No. 168.

Primary Examiner—John Doll
Assistant Examiner—Susan L. Futrovsky
Attorney, Agent, or Firm—Banner, Birch, McKie & Beckett

[57] ABSTRACT

The present invention is directed to monoclonal antibodies, and hybridomas which produce them, which are preferentially reactive with canine lymphoma cells and insignificantly reactive with normal canine lymphocytes.

10 Claims, No Drawings

MONOCLONAL ANTIBODIES AGAINST LYMPHOMA-ASSOCIATED ANTIGENS, HYBRID CELL LINES PRODUCING THESE ANTIBODIES

This application is a continuation of U.S. Ser. No. 044,285, filed Apr. 30, 1987.

BACKGROUND OF THE INVENTION

1. Field of the Invention

This invention is directed to monoclonal antibodies against antigens associated with lymphoma, hybrid cell lines producing these antibodies, and methods of using these monoclonal antibodies.

2. Description of the Background Art

The lymphomas are a group of malignant diseases of lymphoreticular origin which arise in the lymph nodes or in the lymphoid tissues of parenchymal organs such as the gut, lung, or skin. In humans, 90% of cases of Hodgkin's disease originate in lymphnodes, whereas the remaining 10% are of extranodal origin. Human non-Hodgkin's lymphomas, of ten involve tissues of parenchymal organs with 60% of these lymphomas originating in the lymphnodes and 40% having an extranodal origin.

In the dog, lymphoma is the most common hemopoietic tumor. It is an autochthonous, spontaneously occurring neoplasm in an outbred animal. Most dogs with lymphoma present generalized lymphadenophathy and hepatosplenomegaly. Other sites of involvement include anterior mediastinal, pulmonary, intestinal, cutaneous lymphnodes and other extranodal forms. (Dorn, et al., *American Journal of Veterinary Research*, 28: 993, 1967). The histological classification is that of the poor prognosis types which are found in man (Bloomfield, et al., *New England Journal of Medicine*, 301: 512, 1979). Based on the National Cancer Institute Working Formulation For Human Lymphoma Pathologic Classification (The Non-Hodgkins Lymphoma Pathologic Classification Project, *Cancer*, 49: 2112, 1987), the majority of canine cases would be defined as high grade types. In addition, canine lymphoma responds to the same chemotherapeutic drugs as those used in humans, for example, prednisone, cyclophosphamide, vincristine, doxorubicin and L-asparaginase (Macewen, et al., *Journal Of The American Veterinary Medical Association*, 178: 1178, 1981).

Canine lymphoma resembles human non-Hodgkins lymphoma in pathological presentation, response of tumor cells to the same cytotoxic agents, correlation of immunophenotyping of cell surface markers to histological classification and response to therapy, and in distribution of B, T, and non-T, non-B cell lymphomas (Applebaum, et al., *Hematology And Oncology*, 2: 151, 1984; Carter, et al., *Canadian Journal Of Veterinary Research*, 50: 154, 1986). Canine lymphoma, therefore, represents a good model for comparative studies with human lymphoma due to the close behavioral similarities of lymphoma seen in these species.

SUMMARY OF THE INVENTION

It is an object of the present invention to provide a monoclonal antibody that is capable of reacting with canine lymphoma cells for purposes of effective diagnosis and therapy of lymphomatous disease.

Another object of the present invention is to produce monoclonal antibodies that are capable of reacting with canine lymphoma cells, but show insignificant reactivity with normal canine lymphocytes.

It is another object of the present invention to provide methods for the in vitro and in vivo diagnosis of lymphoma using monoclonal antibodies which react with canine lymphoma cells.

Still another object of the invention is to provide methods for suppressing lymphomatous disease in a canine using unlabeled or therapeutically labeled monoclonal antibodies which react with lymphoma cells.

The present invention thus relates to monoclonal antibodies reactive with canine lymphoma cells, but which are insignificantly reactive with normal canine lymphocytes. The invention further includes hybrid cell lines which produce these antibodies as well as methods of using and processes of pairing these monoclonal antibodies.

Present therapeutic approaches to the treatment of dog lymphoma are generally unsuccessful. Regretably, monoclonal antibodies described thus far have been produced by immunization with normal canine cells thereby greatly limiting their potential therapeutic efficacy. Hence, a strong need exists for monoclonal antibodies which will react with lymphoma cells, but have no significant reactivity with normal canine lymphocytes.

The ability to preferentially react with lymphoma cells while at the same time showing no significant reactivity with normal lymphocytes is very significant in terms of the detection of lymphoma and the immunotherapeutic use of these monoclonal antibodies. By preferentially reacting with lymphoma cells, while at the same time showing insignificant reactivity towards normal lymphocytes, the monoclonal antibodies of the invention will have a minimal detrimental side effect on the normal lymphocyte population when used immunotherapeutically. This specificity will, in turn, result in greater accuracy when the monoclonal antibodies of the invention are used immunodiagnostically.

DETAILED DESCRIPTION

The present invention relates to monoclonal antibodies for antigen indicative of lymphoma. These monoclonal antibodies are highly useful for both the in vitro and in vivo immunological detection of antigens associated with lymphoma and for the immunotherapeutic eradication of lymphomas bearing these antigens.

The general method used for production of hybridomas secreting monoclonal antibodies is well known to those of ordinary skill in the art. Illustrative of the techniques utilized in the present invention are those descrlbved in *Proceedings of the National Academy of Science, USA*, 75: 3405, (1978) and Koprowski, U.S. Pat. No. 4,172,124 entitled "Method of Producing Tumor Antibodies."

In brief, female BALB/c were immunized with canine lymphoma cells (17-71) and later boosted with the same cell line. After 4 days, the animals were sacrificed and spleen cells fused with a mouse non-secretor myeloma cell line. Hybridomas were screened for antibody production and positive clones were tested for monoclonal antibody binding to various target cells.

The isolation of other hybridomas secreting monoclonal antibodies with the specificity of the monoclonal antibodies of the invention can be accomplished by one of ordinary skill in the art by producing anti-idiotypic antibodies (Herlyn, et al., *Science*, 232:100, 1986). An anti-idiotypic antibody is an antibody which recognizes unique determinants present on the monoclonal antibody produced by the hybridoma of interest. These determinants are located in the hypervariable region of the antibody. It is this region which binds to a given epitope and, thus, it is responsible for the specificity of the antibody. The anti-idiotypic antibody can be prepared by immunizing an animal with the monoclonal antibody of interest. The animal immunized will recognize and respond to the idiotypic determinants of the immunizing antibody by producing an antibody to these idiotypic determinants. By using the anti-idiotypic antibodies of the second animal, which are specific for the monoclonal antibodies produced by a single hybridoma which was used to immunized the second animal, it is now possible to identify other clones with the same idiotype as the antibody of the hybridoma used for immunization.

Idiotypic identity between monoclonal antibodies of two hybridomas demonstrates that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity.

Alternatively, it is possible to evaluate, without undue experimentation, a monoclonal antibody to determine whether it has the same specificity of as monoclonal antibody of the invention by determining whether the monoclonal antibody being tested prevents the monoclonal antibody of the invention from binding to a particular antigen, or cell line, with which the monoclonal antibody of the invention is normally reactive. If the monoclonal antibody being tested competes with the monoclonal antibody of the invention, as shown by a decrease in binding by the monoclonal antibody of the invention, then it is likely that the two monoclonal antibodies bind to the same epitope. Also, if the monoclonal antibody in question showed the same low level of reactivity for normal lymphocytes as seen with the antibody of the invention then it is likely that the two antibodies have the same specificity.

While the in vivo use of monoclonal antibody from a foreign donor species in a different host recipient species is usually uncomplicated, a potential problem which may arise is the appearance of an adverse immunological response by the host to antigenic determinants present on the donor antibody. In some instances, this adverse response can be so severe as to curtail the in vivo use of the donor antibody in the host. Further, the adverse host response may serve to hinder the lymphoma-suppressing efficacy of the donor antibody. One way in which it is possible to circumvent the likelihood of an adverse immune response occurring in the host is by using chimeric antibodies (Sun, et al., *Hybridoma*, 5 (*Supplement* 1): S17, 1986; Oi, et al., *Bio Techniques*, 4 (3): 214, 1986). Chimeric antibodies are antibodies in which the various domains of the antibodies heavy and light chains are coded for by DNA from more than one species. Typically, a chimeric antibody will comprise the variable domains of the heavy ($V_H$) and light ($V_L$) chains derived from the donor species producing the antibody of desired antigen specificity and the constant antibody domains of the heavy ($C_H$) and light ($C_L$) chains derived from the host recipient species. It is believed that by reducing the exposure of the host immune system to the antigenic determinants of the donor antibody domains, especially those in the $C_H$ region, the possibility an adverse immunological response occurring in the recipient species will be reduced. Thus, for example, it is possible to produce a chimeric antibody for in vivo clinical use in canines which comprises mouse $V_H$ and $V_L$ domains coded for by DNA isolated from ATCC HB 9401, ATCC HB 9402, or ATCC HB 9403 and $C_H$ and $C_L$ domains coded for by DNA isolated from a canine cell.

Under certain circumstances, monoclonal antibodies of one isotype might be more preferable than those of another in terms of their diagnostic or therapeutic efficacy. For example, it is known that unmodified mouse monclonal antibodies of isotype gamma-2a and gamma-3 are generally more effective in inhibiting the growth of tumors than are antibodies of the gamma-1 isotype. This differential efficacy is thought to be due to the ability of the gamma-2a and gamma-3 isotypes to more actively participate in the cytolytic destruction of tumor cells. Particular isotypes of a monoclonal antibody can be prepared either directly, by selecting from the initial fusion, or prepared secondarily, from a parental hybridoma secreting monoclonal antibody of different isotype by using the sib selection technique to isolate class-switch variants (Steplewski, et al., *Proceedings of National Academy of Science, USA*, 82: 8653, 1985; Spira, et al., *Journal of Immunological Methods*, 74: 307, 1984). Thus, the monoclonal antibodies of the invention would include class-switch variants having the specificity of monoclonal antibodies 231, 234 (1) and 234 (2a) which are produced by ATCC HB 9401, ATCC HB 9402, and ATCC HB 9403, respectively.

The monoclonal antibodies of the invention can be used in any animal in which it is desirable to administer in vitro or in vivo immunodiagnosis or immunotherapy. The term "animal" as used herein is meant to include both humans as well as non-humans.

The term "antibody" as used in this invention is meant to include intact molecules as well as fragments thereof, such as, for example, Fab and F(ab')$_2$, which are capable of binding the epitopic determinant.

The monoclonal antibodies of the invention are particularly suited for use in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Alternatively, the appropriately labelled monoclonal atibodies of the invention can be used to diagnose lymphoma in vitro by using flow cytometry and cell sorting instruments.

The monoclonal antibodies of the invention can be bound to many different carriers and used to detect the presence of lymphoma-associated antigen. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibody, or will be able to ascertain such, using routine experimentation.

There are many different labels and methods of labeling known to those of ordinary skill in the art. Examples of the types of labels which can be used in the present invention include enzymes, radioisotopes, fluorescent compounds, chemiluminescent compounds, and bioluminescent compounds. Those of ordinary skill in the art will know of other suitable labels for binding to the monoclonal antibody, or will be able to ascertain such, using routine experimentation. Furthermore, the binding of these labels to the monoclonal antibody of the invention can be done using standard techniques common to those of ordinary skill in the art.

For purposes of the invention, the lymphoma-associated antigen which is detected by the monoclonal antibodies of the invention may be present in biological fluids and tissues. Any sample containing a detectable amount of lymphoma-associated antigen can be used. Normally, a sample is a liquid such as urine, saliva, cerebrospinal fluid, blood, serum and the like, or a solid or semi-solid such as tissues, feces, and the like.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, pyridoxal, and fluoresceine, which can react with specific anti-hapten antibodies.

As used in this invention, the term "epitope" is meant to include any determinant capable of specific interaction with the monoclonal antibodies of the invention. Epitopic determinants usually consist of chemically active surface groupings of molecules such as amino acids or sugar side chains and usually have specific three dimensional structural characteristics, as well as specific charge characteristics.

In using the monoclonal antibodies of the invention for the in vivo detection of antigen, the detectably labeled monoclonal antibody is given in a dose which is diagnostically effective. The term "diagnostically effective" means that the amount of detectably labeled monoclonal antibody is administered in sufficient quantity to enable detection of the site having the antigens for which the monoclonal antibodies are specific. The concentration of detectably labeled monoclonal antibody which is administered should be sufficient that the binding to the tumor site is detectable compared to the background signal. Further, it is desirable that the detectably labeled monoclonal antibody be rapidly cleared from the circulatory system in order to give the best tumor-to-background signal ratio.

As a rule, the dosage of detectably labeled monoclonal antibody for diagnosis will vary depending on such factors as age, sex and extent of disease of the individual. The dosage of monoclonal antibody can vary from 0.01 mg/m$^2$ to 20 mg/m$^2$, preferably 0.1 mg/m$^2$ to 10 mg/m$^2$.

For diagnostic in vivo imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

For in vivo diagnosis radioisotopes may be bound to immunoglobin either directly or indirectly by using an intermediate functional group. Intermediate functional groups which often are used to bind radioisotopes which exist as metallic ions to immunglobins are the bifunctional chelating agents diethylenetriaminepentaacetic acid (DTPA) and ethylenediaminetetraacetic acid (EDTA).

The antibodies of the invention can also be labeled with a paramagnetic isotype for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for NMR.

The invention monoclonal antibodies can be used to monitor the course of malignant disease in an individual. Thus, by measuring the increase or decrease in the size or number of malignant sites, or changes in the concentration of antigen shed into various body fluids, it would be possible to determine whether a particular therapeutic regimen aimed at ameliorating the malignancy is effective.

The monoclonal antibodies of the invention can also be used alone, as mixtures of monoclonal antibodies of various epitopic specificities, or in combination with effector cells, for immunotherapy in an animal having a tumor which expresses lymphoma-associated antigens with epitopes reactive with the monoclonal antibodies of the invention. When used in this manner the dosage can vary from about 10 mg/m$^2$ to about 2000 mg/m$^2$. The term "therapeutically effective" means that the amount of antibody used is of sufficient quantity to ameliorate the cause of disease due to the malignancy.

The term "preferentially reactive" means that the monoclonal antibodies of the invention are more likely to bind to a lymphoma cell than they are to a normal lymphocyte. Generally, the monoclonal antibodies of the invention will bind at least twice as frequently to lymphoma cells as they will to normal lymphocytes.

The term "insignificantly reactive" means that the degree of reactivity seen between the monoclonal antibody of the invention and normal lymphocytes does not hinder either the diagnostic or therapeutic usefulness of the monoclonal antibody. For example, when used diagnostically the monoclonal antibodies of the invention bind so much more significantly to lymphoma cells as compared to normal tissue that the malignant tissue is clearly distinguishable from any background due to binding of the antibodies to non-lymphomatous tissue. Alternatively, when the antibodies of the invention are used immunotherapeutically no significant destruction of non-lymphomatous tissue occurs at concentrations of antibody which are therapeutically effective in suppressing the lymphoma. In general, the monoclonal antibodies of the invention will be insignificantly reactive with cells having less than about $3 \times 10^5$ antibody binding sites.

When used for immunotherapy, the monoclonal antibodies of the invention may be unlabeled or labeled with a therapeutic agent. These agents can be coupled either directly or indirectly to the monoclonal antibodies of the invention. One example of indirect coupling is by use of a spacer moiety. These spacer moieties, in turn, can be either insoluble or soluble (Diener, et al., *Science*, 231: 148, 1986) and can be selected to enable drug release from the monoclonal antibody molecule at the target site. Examples of therapeutic agents which can be coupled to the monoclonal antibodies of the invention for immunotherapy are drugs, radioisotopes, immunomodulators, lectins and toxins.

The drugs which can be conjugated to the monoclonal antibodies of the invention include non-proteinaceous as well as proteinaceous drugs. The term "non-proteinaceous drugs" encompasses compounds which are classically referred to as drugs such as for example, mitomycin C, daunorubicin, and vinblastine.

The proteinaceous drugs which the monoclonal antibodies of the invention can be labeled include immunomodulators and other biological response modifiers. The term "biological response modifiers" is meant to encompass substances which are involved in modifying the immune response in such manner as to enhance the destruction of the tumor cells bearing the antigen for which the monoclonal antibodies of the invention are specific. Examples of immune response modifiers include such compounds as lymphokines. Examples of lymphokines include tumor necrosis factor, interleukins 1, 2, and 3, lymphotoxin, macrophage activating factor, migration inhibition factor, colony stimulating factor and interferon. Interferons with which the monoclonal antibodies of the invention can be labeled include alpha-interferon, beta-interferon, and gamma-interferon and their subtypes.

In using radioisotopically conjugated monoclonal antibodies of the invention for immunotherapy certain isotypes may be more preferable than others depending on such factors as tumor distribution and mass as well as isotype stability and emission. If desired, the tumor distribution and mass can be evaluated by the in vivo diagnostic techniques described supra. Depending on the type of malignancy present some emitters may be preferable to others. In general, alpha and beta particle-emitting radioisotopes are preferred in immunotherapy. For example, if an animal has solid tumor foci a high energy beta emitter capable of penetrating several millimeters of tissue, such as $^{90}Y$, may be preferable. On the other hand if the malignancy consists of single target cells, as in the case of leukemia, a short range, high energy alpha emitter such as $^{212}Bi$ may be preferred. Examples of radioisotopes which can be bound to the monoclonal antibodies of the invention for therapeutic purposes are $^{125}I$, $^{131}I$, $^{90}Y$, $^{67}Cu$, $^{212}Bi$, $^{211}At$, $^{212}Pb$, $^{47}Sc$, $^{109}Pd$, $Au^{199}$ and $^{188}Re$.

Lectins are proteins, usually isolated from plant material, which bind to specific sugar moieties. Many lectins are also able to agglutinate cells and stimulate lymphocytes. However, ricin is a toxic lectin which has been used immunotherapeutically. This is accomplished by binding the alpha-peptide chain of ricin, which is responsible for toxicity, to the antibody molecule to enable site specific delivery of the toxic effect.

Toxins are poisonous substances produced by plants, animals, or microorganisms that, in sufficient dose, are often lethal. Diphtheria toxin is a substance produced by *Corynebacterium diphtheriae* which can be used in this manner. This toxin consists of an alpha and beta subunit which under proper conditions can be separated. The toxic A component can be bound to antibody and used for site specific delivery to a tumor expressing the antigens for which the monoclonal antibodies of the invention are specific.

Other therapeutic agents which can be coupled to the monoclonal antibodies of the invention are known, or can be easily ascertained, by those of ordinary skill in the art.

The labelled or unlabelled monclonal antibodies of the invention can also be used in combination with therapeutic agents such as those described supra. Especially preferred are therapeutic combinations comprising the monoclonal antibody of the invention and immunomodulators and other biological response modifiers.

Thus, for example, the monoclonal antibodies of the invention can be used in combination with alpha-interferon. This treatment modality enhances monoclonal antibody targeting of tumors by increasing the expression of monoclonal antibody reactive antigen by the cancer cells (Greiner, et al., *Science*, 235:895, 1987). Alternatively, the monoclonal antibody of the invention could be used, for example, in combination with gamma-interferon to thereby activate and increase the expresion of Fc receptors by effector cells which, in turn, results in an enhanced binding of the monoclonal antibody to the effector cell and killing of target tumor cells. Those of skill in the art will be able to select from the various biological response modifiers to create a desired effector function which enhances the efficacy of the monoclonal antibody of the invention.

When the labelled or unlabelled monoclonal antibody of the invention is used in combination with unbound therapeutic agents, such as those described herein, the administration of the monoclonal antibody and the therapeutic agent usually occurs sequentially. The term "sequentially" means that the monoclonal antibody and the unbound therapeutic agent are administered reasonably close together with respect to time. Usually, it is preferred to administer the unbound therapeutic agent before the monoclonal antibody. For example, the unbound therapeutic agent can be administered 1 to 6 days before the monoclonal antibody. The administration of the unbound therapeutic agent can be, daily or at any other interval depending upon such factors, for example, as the nature of the tumor, the condition of the patient and half-life of the agent.

In another therapeutic aspect, the monoclonal antibodies of the invention, either singly or in combination, can be pre-incubated with recipient leucocytes, especially monocytes, and the monoclonal antibody/leucocyte mixture introduced into the animal undergoing therapy (Douillard, et al., *Hybridoma (Supplement 1)*, 5, S137, 1986).

Using the monoclonal antibodies of the invention, it is possible to design therapies combining all of the characteristics described herein. In a given situation it may be desirable to administer an unbound therapeutic agent, or agents, prior to the administration of therapeutically labelled or unlabelled monoclonal antibodies of the invention in combination with effector cells and the same, or different, therapeutic agent or agents. For example, it may be desirable to treat an animal with lymphoma by first administering gamma-interferon and interleukin-2 daily for 3 to 5 days, and on day 5 administer the monoclonal antibody of the invention in combination with effector cells as well as gamma-interferon, and/or interleukin-2.

It is also possible to utilize liposomes with the monoclonal antibodies of the invention in their membrane to specifically deliver the liposome to the area of the tumor expressing antigens reactive with the monoclonal antibodies of the invention. These liposomes can be produced such that they contain, in addition to the monoclonal antibody, such immunotherapeutic agents as those described above which would then be released at the tumor site (Wolff, et al., *Biochemica et Biophysica Acta*, 802: 259, 1984).

The dosage ranges for the administration of the monoclonal antibodies of the invention are those large enough to produce the desired effect in which the symptoms of the tumor are ameliorated. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications, immune tolerance or similar conditions. Dosage can vary from about 0.1 mg/m$^2$ to about 2000 mg/m$^2$, preferably from about 0.1 mg/m$^2$ to about 500 mg/m$^2$/dose, in one or more dose administrations daily, for one or several days. Generally, when the monoclonal antibodies of the invention are administered conjugated with therapeutic agents, lower dosages, such as those used for in vivo diagnostic imaging, can be used.

The antibodies can be administered parenterally by injection or by gradual perfusion over time. The monoclonal antibodies of the invention can be administered intravenously, intraperitoneally, intramuscularly, subcutaneously, intracavity, or transdermally, alone or in combination with effector cells.

Preparations for parenteral administration include sterile aqueous or non-aqueous solutions, suspensions, and emulsions. Examples of non-aqueous solvents are propylene glycol, polyethylene glycol, vegetable oils such as, olive oil, and injectable organic esters such as ethyl oleate. Aqueous carriers include water, alcoholic-/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, and inert gases and the like.

It is to be understood that all of various therapeutic and diagnostic uses discussed supra, as well as the many other uses known or readily discernable to those of skill in the art, can utilize combinations of monoclonal antibodies having the specificity of monoclonal antibodies 231, 234(1) or 234(2a).

The invention also relates to a method for preparing a medicament or pharmaceutical composition comprising the monoclonal antibodies of the invention, the medicament being used for therapy of tumors expressing antigens reactive with the monoclonal antibodies of the invention.

Monoclonal antibodies 231, 234(1) and 234(2a) can be utilized in the present invention. 231 is obtained from, or has the identifying characteristics of, an antibody obtained from the cell line having ATCC accession number HB 9401. 234(1) is obtained from, or has the identifying characteristics of, an antibody obtained from the cell line having ATCC accession number HB 9402. 234(2a) is obtained from, or has the identifying characteristics of, an antibody obtained from the cell lne having ATCC accession number HB 9403. These cell lines were placed on deposit for 30 years at the American Type Culture Collection (ATCC) in Rockville, Md. prior to Apr. 30, 1987.

The above disclosure generally describes the present invention. A more complete understanding can be obtained by reference to the following specific examples which are provided herein for purposes of illustration only, and are not intended to limit the scope of the invention.

EXAMPLE 1

PREPARATION OF HYBRIDOMA CELL LINES PRODUCING MONOCLONAL ANTIBODIES TO CANINE LYMPHOMA

A. Immunization And Production of Hybridomas

Female BALB/c mice were immunized intraperitoneally with $2 \times 10^7$ 17-71 canine lymphoma cells and two weeks later injected intravenously with $1 \times 10^6$ cells. Four days after the second injection, the mice were sacrificed and their spleens aseptically separated. A spleen cell suspension was prepared as described in Koprowski, et al., *Proceedings of the National Academy of Science, USA*, 74: 2985 (1977). Immune splenocytes were fused with mouse myeloma cell lines P3X63-Ag8.653 (Kearney, et al., *Journal of Immunology*, 123: 1548, 1979) or SP2/0-Ag14 (Shulman, et al., *Nature*, 276: 269, 1978), as described in Koprowski, et al., Ibid. Fused cells were suspended in hypoxanthine/aminopterin/thymidine medium and seeded in 24-well tissue culture plates using a feeder layer. Approximately 3 weeks after fusion, single colonies were picked from each well and tested for immunoglobian production. Secreting hybridomas were cloned and their producted tested for binding to various target cells.

B. Determination of Immunoglobulin Isotype

Isotype determinations were made using a 2-side amplified enzyme-linked immunosorbent assay (Engvall, et al.; *Immunochemistry*, 8: 871, 1971; Lehtone, et al., *Journal of Immunological Methods*, 34: 61, 1980).

C. Selection of Monoclonal Antibodies

More than 600 hybridoma colonies were established from 4 consecutive fusions; 6 hybridomas were selected, which in preliminary analysis by RIA had restricted binding specificity (Table 1).

TABLE 1

| Monoclonal Antibody Binding in Radioimmunoassay | | | |
|---|---|---|---|
| | | Established cell lines | |
| MAb | | Canine lymphoma | Human | Bone marrow fibroblast |
| Code | Isotype | 17-71 | Raji | (dog) |
| 231 | IgG2a | 5000$^a$ | 0 | 110 |
| 234 | IgG1 | 5660 | 0 | 530 |
| 254 | IgG3 | 5450 | 0 | 0 |
| 212 | IgG1 | 8470 | 0 | 130 |
| 215 | IgM | 6650 | 0 | 0 |
| 216-1 | IgM | 4675 | 2400 | 2260 |

$^a$Represents cpm of triplicate determinations minus P$_3$ background (usually 150–250 cpm).

Of the 6 hybridomas 5 secreted monoclonal antibodies (MAbs) that bound to 17-71 cells and did not bind to human Burkitt's lymphoma Raji cells. Antibody 216-1 bound to 17-71, Raji cells and to canine fibroblasts. MAb 234 showed some crossreactivity with bone marrow-derived fibrolasts.

EXAMPLE 2

GENERAL ANALYTIC TECHNIQUES

A. Preparation of Cell Suspensions

Lymph nodes were surgically excised from dogs with histologically confirmed lymphoma and placed in MEM. Lymph nodes were minced and passed through a sieve (E-C Cellector) using a syringe plunger and collected into MEM. Cells were washed once with cold phosphate-buffered saline (PBS) and used immediately for fluorescent activated cell sorter (FACS) analysis. White blood cells were purified from heparinized dog or human blood by centrifugation through Ficoli-Paque (Bayum, *Nature*, 204: 793, 1964). Dog fibroblasts were obtained by culture of lymph node or bone marrow cells suspended in MEM/10% FBS and adherence techniques. Cells were treated with trypsin-EDTA for 2-3 minutes and washed with PBS.

B. Immunoperoxidase Assay

Tissue samples from normal and tumor-bearing dogs were cut into small pieces and frozen at $-70°$ C. or fixed in 10% neutral buffered formalin and paraffin embedded by routine procedures. Slides were deparaffinized, hydrated, and washed for 5 minutes in running water. Frozen sections were air dried, fixed in cold acetone for 10 minutes, and washed with water. Endogenous peroxidase was inhibited by treatment with 0.3% $H_2O_2$ in absolute methanol for 15 minutes (Atkinson, et al., *Cancer Research*, 42: 4820, 1982), followed by 10% normal horse serum in PBS for 10 minutes. The immunoperoxidase (IP) assay was performed by a modification of the method of Shu, et al. (*Journal of Histochemistry and Cytochemistry*, 29: 1349, 1981) on 5 um sections with a biotin-avidin kit (Vector Laboratories, Inc., Burlingame, CA). The supernatant of P3-X63Ag8 (Kohler, et al., *Nature*, 256: 495, 1975) or PBS/bovine serum albumin (BSA) buffer was used as a control.

C. Cytofluorimetry (FACS)

Live cells ($5 \times 10^5$ per well) were plated in a U-bottom 96-well plate and incubated for 1 h with 50 ul of MAB (supernatant) at 4° C. on a plate shaker. Cells were washed twice with 0.1% gelatin solution in PBS without $Ca^{2+}$ and $Mg^{2+}$, and 25 ul of goat anti-mouse fluorescein isothiocyanate (FITC)-conjugated IgG (Cappell Laboratories, Cochranville, Pa, USA) as added. The FITC-conjugated serum had previously been adsorbed with a cell suspension of a normal dog lymph node. After a 1 h incubation at 4° C., cells were again washed three times and resuspended in 300 ul of washing buffer. The cell suspension was then analyzed using a Cytofluorograf System 30/50 (Ortho Diagnostic Systems, Inc., Westwood, MA). Cells could be stored for 2 days after fixing with 1% paraformaldehyde for 30 min, prior to the final washes.

D. Radiolabeling and Cell Extraction

Lymphoma 17-71 cells were labeled with $^{125}I$ by the lactoperoxidase-glucose oxidase method (Mitchel, et al., *Molecular Immunology*, 18: 207, 1981) and extracted at 4° C. for 30 min with solubilizing buffer (0.5% Nonidet P40, 140 mM NaCl, 10 mM NaF, 10 mM Tris, 5 mM EDTA, 100 kallikrein IU/ml aprotinin, 1 mM PMSF, pH 7.5). The extract was clarified by centrifugation at 105,000 g for 1 h. Unlabeled cells were similarly extracted and used in immunoblotting.

E. Immunoblotting

After electrophoresis, proteins were transferred to nitrocellulose sheets (Towlin, et al., *Proceedings of the National Academy of Science, USA*, 76: 4350, 1979) in a Trans-Blot chamber (Bio-Rad Laboratories, Richmond, CA). The nitrocellulose blots were soaked in 2% BSA in PBS and 0.1% $NaN_3$ overnight. The sheets were then rinsed with 2% gamma globulin free horse serum in PBS and 0.1% $NaN_3$ (buffer A) and covered with hybridoma supernatant containing MAb for 1 h at room temperature. Sheets were washed three times with buffer A and incubated with $^{125}I$-labeled rabbit and anti-mouse Fab (approximately $2 \times 10^5$ cpm/ml) for 1 h. Nitrocellulose sheets were finally washed four times with buffer A, dried, and exposed to XAR-5 X-ray film (Eastman, Rochester, NY) using an intensifying screen.

F. Immonoprecipation

Aliquots of cleared lysates were incubated with 200 ul of hybridoma supernatant at 4° C. overnight. Immune complexes were precipitated by absorption to 100 ul of anti-mouse IgG-agarose bead suspension (SIGMA Chemical Co. St. Louis, MO). The precipitate was mixed with 60 ul of Laemmli (*Nature*, 227:680, 1970) reducing buffer and boiled for 5 min. The antigens were analyzed by sodium dodecyl sulfate (SDS) polyacrylamide gel electrophoresis.

G. Electrophoresis

Electrophoresis was performed by the method of Laemmli (*Nature*, 227: 680, 1970) using 10% polyacrylamide with 2% SDS. Gels were stained with 0.02% Coomassie brilliant blue R250 in 25% methanol-10% acetic acid, destained with 5% acetic acid and 2% glycerol, dried, and autoradiographed, or transferred to nitrocellulose sheets.

H. Glycolipid Extraction

The total glycolipid fraction from 17-71 cells was prepared by chloroform/methanol extraction followed by separation on a SEP-PAK $C_{18}$ cartridge (Millipore-Waters Ass. Milford, MA). Then 5 ml of chloroform/methanol/water (60:35:8 by vol.) was added to the cell pellet and the mixture sonicated at room temperature for several minutes. After centrifugation, the supernatant was evaporated to dryness using $N_2$. The fraction was redissolved in methanol/water (1:1 v/v) and applied to the SEP-PAK cartridge previously equilibrated in the same solvent. The cartridge was washed with 10 ml water and total gylcolipids eluted with chloroform/methanol (2:1 v/v).

I. Thin-Layer Chromatography

Thin-layer chromatograms were developed on high-performance thin layer chromatography aluminium sheets (10×20 cm) with Silica Gel 60 (Merck, Darmstadt, FRG) using chloroform/methanol/water (60:35:8 by vol.). Anisaldehyde reagent (Karlsson, et al., *Biochimica et Biophysica Acta*, 316: 317, 1973) was used for detection of total glycolipids.

J. Chromatogram Binding Assay

These assays were performed as described elsewhere (Hansson, et al., *Journal of Biological Chemistry*, 258:

4091, 1983). After chromathography, dried chromatograms were immersed in a 0.5% polyisobutylmethacrylate (Plexigum P28, Rohm GmbH, Darmstadt, FRG) solution in ether and air-dried for 5 min. Plates were sprayed and then covered with 2% BSA in PBS and 0.1% $NaN_3$ for 2 h. After removing the albumin solution by tipping the plates, hybridoma supernatants containing MAbs diluted 1:2 were added. The plates were incubated for 2 h in a humidified Petri dish. The antibody solutions were removed and the plates washed five times with PBS and incubated with $^{125}I$-labeled $F(ab')_2$ rabbit anti-mouse Fab (approximately $1 \times 10^6$ cpm/ml) for 1 h. Finally, plates were washed six times with PBS, dried and exposed to XAR-5 X-ray film (Eastman-Kodak) using an intensifying screen.

EXAMPLE 3

Monoclonal Antibody Cross Reactivity With Other Cell Lines

The binding cross reactivity of various anti-canine lymphoma monoclonal antibodies with established cell lines of different species were tested using the RIA technique.

TABLE 2

Crossreactivity Of Monoclonal Antibodies With Established Cell Lines Of Different Species

| MAb | Isotype | Canine lymphoma 17-71 | Rat myeloma Y2Agl.2.3 | Human leukemia/lymphoma | | | | | | | |
|---|---|---|---|---|---|---|---|---|---|---|---|
|  |  |  |  | Raji | Daudi | Molt-4 | HL60 | H5B2 | K562 | Jurkat | U937 |
| 231 | IgG2a | 3845[a] | 0 | 0 | 0 | 0 | 310 | 200 | 390 | 0 | 1720 |
| 234 | IgG1 | 5190 | 0 | 0 | 120 | 140 | 0 | 185 | 130 | 0 | 220 |
| 254 | IgG3 | 2075 | 0 | 0 | 0 | 0 | 0 | 100 | 0 | 0 | 0 |
| 212 | IgG1 | 5265 | 0 | 0 | 0 | 0 | 0 | 0 | 0 | 0 | 270 |
| 215 | IgM | 3060 | 130 | 0 | 200 | 390 | 175 | 625 | 0 | 390 | 200 |
| 216-1 | IgM | 4545 | 2000 | 2400 | 2380 | 2490 | 2860 | 3550 | 2430 | 2410 | 2740 |

[a]Represents cpm of triplicate determination minus $P_3$ background

As shown in Table 2, only MAb 216-1 crossreacted with human and rat cells. Very low level binding to human lymphoblastoid cells was detected for MAbs 215 (6/8), 234 (5/8), and 231 (4/8). The U931 myelomonocytic cell line, which expresses Fc receptors cross reactive with murine IgG2a immunoglobulins, also bound IgG2a MAb 231.

EXAMPLE 4

BINDING OF MONOCLONAL ANTIBODIES TO NORMAL CELLS

The results of FACS analysis of normal canine and human cells are shown in Table 3. Only MAb 212 crossreacted with normal canine lymphocytes at a significant level; MAbs 215 and 234 showed some binding to lymphocytes and the remaining MAbs did not bind to normal canine or human lymphocytes isolated from blood. Four MAbs were clearly positive for binding to canine monocytes and 3 showed some binding to granulocytes. None of the MAbs bound to normal human white blood cells, except MAb 231 which bound to 68.5% of granulocytes. The antibodies were generally negative for cells isolated from canine bone marrow and from spleen. Monoclonal antibodies 212 and 215 showed high levels of binding with lymph node cells, while MAb 234 bound to 48.5% of lymph node-derived lymphocytes. However, in vitro studies have shown that MAb 234 does not kill normal canine lymphocytes.

TABLE 3

FACS Analysis Of MAb Binding To Lymphocytes From Different Sources

| MAb | Isotype | Canine blood | | | Canine | | | Human blood | |
|---|---|---|---|---|---|---|---|---|---|
|  |  | Lymphocyte | Monocyte | Granulocyte | Lymph node | Spleen | Bone Marrow | Lymphocyte | Granulocyte |
| 231 | IgG2a | 8.8[a] | 51.2 | 39.6 | 17.3 | 0.7 | 17.1 | 5.8 | 68.5 |
| 234 | IgG1 | 34.1 | 69.0 | 15.1 | 48.5 | 3.9 | 12.3 | 5.0 | 9.6 |
| 254 | IgG3 | 11.5 | 21.3 | 5.0 | 6.7 | 1.1 | 20.4 | 4.6 | 4.3 |
| 212 | IgG1 | 94.1 | 89.9 | 24.2 | 94.6 | 1.3 | 17.7 | 4.4 | 2.8 |
| 215 | IgM | 34.8 | 60.4 | 8.0 | 93.7 | 2.1 | 17.2 | 5.1 | 3.6 |
| 216-1 | IgM | 5.8 | 12.3 | 7.5 | 8.2 | 1.4 | NT | 6.8 | 5.4 |
| P3X63Ag8 | IgG1 | 1.8 | 14.0 | 6.9 | 5.2 | 1.9 | 15.4 | 4.5 | 4.7 |

NT: Not Tested
[a]Percentage of fluorescent cells

Spleen, liver, and kidney samples were stained using the IP technique described, supra. Monoclonal antibodies 212, 215, and 216-1 showed some cross reactivity with all samples. Monoclonal antibody 254 bound only minimally to liver and kidney, and MAb antibody 234 did not bind to any tissue. Monoclonal antibody 231, of isotype gamma-2a, bound to hepatic duct epithelum cytoplasm only. There was no cell membrane binding in normal tissues tested by IP. Very minimal binding to renal tubule epithelial cells was occasionally observed.

EXAMPLE 5

BINDING OF MONOCLONAL ANTIBODIES TO CANINE LYMPHOMA CELLS

The lymphoma cell line 17-71 used for immunization and 15 different lymphomatous nodes were used for analysis of their phenotypes on the basis of their reactivity with 6 monoclonal antibodies. In addition, 17-71 cells and malignant lymph nodes were analyzed with murine anti-human DR (IgG2a) monoclonal antibody 37-7 and with anti-glycoprotein (IgG2b) monoclonal antibody 480-1-4, which reacts with all human tissues (Table 4).

Human DR antigens, encoded by the HLA-D region, are thought to be analogous to the Ia antigens in mouse, encoded by the major histocompatibility complex. Moreover, a bimolecular complex comprising a 29 KD and a 34 KD polypeptide has been found in canine cell membranes which is cross-reactive with the human DR antigens. See Deeg, et al., Immunogenetics, vol. 16, pp. 445–457, 1982.

TABLE 4

Reactivity Of Monoclonal Antibodies to Canine Lymphomatous Nodes

| MAb Code | Isotype | 17-71 Cells | Canine lymphoma nodes | | | | | | | | | | | | | |
|---|---|---|---|---|---|---|---|---|---|---|---|---|---|---|---|---|
| | | | 1 | 2 | 3 | 4 | 5 | 6 | 7 | 8 | 9 | 10 | 11 | 12 | 13 | 14 | 15 |
| 231 | IgG2a | 65.0[a] | 93.0 | 22.3 | 3.6 | 3.2 | 33.2 | 74.2 | 53.8 | 23.6 | 30.0 | 29.7 | 16.5 | 19.9 | 62.9 | 5.3 | 84.6 |
| 234 | IgG1 | 88.4 | 72.1 | 76.1 | 2.0 | 54.4 | 11.3 | 27.7 | 54.8 | 22.7 | 22.3 | 6.5 | 11.7 | 33.9 | 8.0 | 0.8 | 71.8 |
| 254 | IgG3 | 26.5 | 1.8 | 21.0 | 2.1 | 28.6 | 2.2 | 8.4 | 22.3 | 31.3 | 8.1 | 8.0 | 13.3 | 10.4 | 8.4 | 0.6 | 8.1 |
| 212 | IgG1 | 96.8 | 99.8 | 9.4 | 80.7 | 82.3 | 94.1 | 98.2 | 88.5 | 96.3 | 86.8 | 68.9 | 76.9 | 28.8 | 9.2 | 94.9 | 95.9 |
| 215 | IgM | 96.8 | 99.8 | 11.4 | 76.8 | 84.5 | 86.2 | 96.2 | 77.5 | 86.6 | 67.7 | 81.5 | 94.0 | 30.0 | 12.0 | 84.8 | 97.6 |
| 216-1 | IgM | 3.9 | 4.9 | 25.3 | 10.7 | 14.2 | 35.9 | 24.7 | 60.5 | 67.7 | 29.0 | 73.3 | 85.1 | 29.1 | 6.0 | 0.3 | 8.0 |
| 37-7 | IgG2a | 60.6 | NT | NT | NT | NT | NT | NT | 85.3 | 90.7 | 80.6 | 72.8 | 83.4 | 21.2 | 57.6 | 75.7 | 90.9 |
| 480-1-4 | IgG2b | NT | NT | NT | NT | NT | NT | NT | 22.2 | NT | 6.2 | 4.9 | 9.2 | 3.2 | NT | 15.8 | 16.9 |
| P3X63AG8 | IgG2 | 1.1 | 1.0 | 5.2 | 3.0 | 4.5 | 3.0 | 4.0 | 7.0 | NT | 19.7 | 4.9 | 9.9 | 6.0 | 1.0 | 5.3 | 1.0 |

NT: Not Tested
[a]Percentage positive cells

FACS analysis of subpopulations of lymphocytes freshly isolated from lymphomatous canine lymph nodes indicated a differential distribution of binding in different animals. All 6 monoclonal antibodies bound to tumor cells contained in 2 lymph nodes. Except for MAb 254, all MAbs bound to 4 lymph nodes samples. Of the six monoclonal antibodies, 4 bound to tumor cells derived from 2 lymph nodes. The remaining 6 canine lymph node-derived tumor cells had binding with dissimilar patterns, 2 of which were reactive only with MAbs 212 and 215, which may be directed against DR-related molecules. The results of this study are summarized in Table 5.

TABLE 5

Summary Of Monoclonal Antibody Reactivity With Lymphomatous Canine Lymph Nodes

| MAb | Ratio Positive/total | % |
|---|---|---|
| 231 | 11/15 | 73.3 |
| 234 | 10/15 | 66.6 |
| 254 | 4/15 | 26.7 |
| 212 | 13/15 | 86.6 |
| 215 | 13/15 | 86.6 |
| 216-1 | 10/15 | 66.6 |

Of the 9 lymph nodes screened with anti-DR MAb 37-7, all showed binding reactivity comparable to MAbs 212 and 215, suggesting that these 2 monoclonal antibodies may be directed against DR molecules on canine lymphocytes.

At least three of these MAbs have unique binding specificities to canine lymphoma. MAb 231 (IgG2a) bound to 73% of lymphomas tested. This antibody is cytotoxic in antibody-dependent cell cytotoxity test (data not shown) and should be an effective immunotherapeutic agent (Herlyn, et al. *Proceedings of the National Academy of Science, USA,* 79: 4761, 1982; Steplewski, et al., *Hybridoma,* 2: 1, 1983). The minimal cross reactivity of MAb 231 observed with the human U937 myelomonocytic cell line and with monocytes and granulocytes is probably due to the binding of IgG2a protein to the Fc receptors expressed by these cells (Akiyama, et al., *Cancer Research,* 44: 5127, 1984). MAb 234 (IgG1) also has restricted specificity, binding to about 70% of canine lymphomas. The immunotherapeutic efficacy of this monoclonal antibody can be further enhanced by selecting an isotype gamma-2a switch variant (Spira, et al., *Journal of Immunological Method,* 74: 307, 1984). The third antibody, MAb 254 (IgG3) bound about 27% of the lymphomas tested, but shows a restricted binding specificity. This MAb is also capable of being improved immunotherapeutically by selecting for the gamma-2a switch variant. In addition, MAb should be of therapeutic value by being capable of binding to lymphomas which are negative for MAbs 231 and 234. In addition, these monoclonal antibodies can be used as diagnostic classification tools in characterizing lymphomas.

EXAMPLE 6

ANTIGEN ANALYSIS

As shown in Table 6, monoclonal antibodies 212 (IgG1) and 215 (IgM) immunoprecipitated a 29 Kd protein. MAb 234 (IgG1) immunoprecipitated a 36 Kd protein. In these studies, MAbs 231 (IgG2a), 254 (IgG3), and 216-1 (IgM) did not bind to immunoblots of tumor cell extracts and no protein molecules were immunoprecipitated from the tumor or normal cells. No binding of these monoclonal antibodies to the glycolipid extracts of tumor and normal cells was detected.

TABLE 6

Antigens Detected by Anti-Canine Lymphoma Monoclonal Antibodies

| Antibody | Antigen detected | |
|---|---|---|
| | Immunoprecipitation | Glycolipid fractions |
| 231 | None | Negative |
| 234 | 36 × 10³ daltons | Negative |
| 254 | None | Negative |
| 212 | 29 × 10³ daltons | Negative |
| 215 | 29 × 10³ daltons | Negative |
| 216-1 | None | Negative |

MAbs 212 and 215 appear to detect a canine Ia-like or DR antigen with a molecular weight of 29 Kd. Eight of 9 dogs screened with MAb 37-7, a murine anti-human DR antibody, and with MAbs 212 and 215 showed similar binding patterns, suggesting that the common target of these monoclonal antibodies is an Ia-like molecule.

EXAMPLE 7

ANTIBODY-DEPENDENT CELL-MEDIATED CYTOTOXICITY (ADCC)

Peripheral blood leucocytes (PBL) were obtained by separation of normal canine heparinized blood over a Ficoll-Hypaque gradient (Atkinson, et al., *Experimental Hematology,* 8:821, 1980). Interface cells were washed three times with PBS without $Ca^{+2}$ and $Mg^{+2}$, and resuspended in RPMI 1640/10% FBS medium containing 20 mM glutamine and penicillin (100 U/ml) and streptomycin (100 ug/ml). Enriched monocyte fractions were obtained by adherence selection of PBL on gelatin-fibronectin-coated flasks as described (Freundlich, et al., *Journal of Immunological Methods,* 62: 31, 1983). Nonadherent leucocytes (lymphocytes) were obtained following 1 hour adsorption on gelatin-fibronectin-coated plastic flasks.

In performing the ADCC assay, tumor cell suspensions were pelleted in a 15 ml tube and labeled with ($^{111}$In)-Indium-oxine (Wiltrout, et al., in *Manual of Macrophage Methodology*, Marcel Dekker, Inc., New York and Basel, 1981) (indium oxyquinoline 1 mCi/ml, Amersham), using 10 uCi/1×10$^6$ cells for 10 minutes. Labeled cells were added in triplicates to U-bottom 96-well Costar ® microtiter plates at 1×10$^4$ cells/well in RPMI 1640/10% FBS medium. 100 ul of purified MAb was added to give a final concentration of 100 ug/ml, or 100 ul of MAb-containing tissue culture supernatant. Anti-influenza MAb (H24B5) of the IgG2a subclass was used as negative control. Effector cells were added at a Target/Effector (T/E) ratio of 1/20. Plates were covered and incubated at 37° C., 5% CO$_2$ and 95% air for 18 hours.

TABLE 7

Antibody-Dependent Cell-Mediated Cytotoxicity (ADCC) of 17-71 Cells with MAb and Various Effector Cells from Different Donors

| MAb | | PBL CELL DONOR | | | | | LYMPHOCYTES CELL DONOR | | | | | MONOCYTES CELL DONOR | | | | |
|---|---|---|---|---|---|---|---|---|---|---|---|---|---|---|---|---|
| Code | Isotype | 11 | 12 | 13 | 14 | 15 | 11 | 12 | 13 | 14 | 15 | 11 | 12 | 13 | 14 | 15 |
| H24B5 | IgG2a | 0.9 | 0.0 | 2.0 | 0.0 | 11.6 | 3.2 | 0.0 | 2.2 | 1.1 | 11.3 | 8.3 | 0.0 | 2.0 | 2.4 | 11.8 |
| 231 | IgG2a | 16.1 | 17.2 | 9.4 | 0.0 | 15.6 | 12.5 | 12.9 | 13.4 | 0.0 | 11.3 | 12.3 | 29.2 | 32.0 | 2.5 | 22.3 |
| 234 | IgG1 | 3.5 | 14.3 | 5.8 | 0.0 | 21.9 | 11.2 | 21.1 | 10.3 | 0.0 | 17.6 | 6.2 | 20.9 | 24.9 | 3.3 | 18.4 |
| 234 | IgG2a | 52.9 | 40.8 | 10.8 | 0.0 | 21.7 | 40.0 | 20.0 | 18.1 | 0.6 | 26.2 | 29.0 | 45.0 | 36.2 | 4.2 | 47.8 |
| 254 | IgG3 | — | 11.8 | 4.2 | 2.2 | 12.8 | — | 11.8 | 6.4 | 0.0 | 11.1 | — | 37.0 | 11.9 | 1.7 | 15.3 |
| 212 | IgG1 | — | 10.9 | 8.0 | 0.0 | 18.7 | — | 12.5 | 11.6 | 0.0 | 22.9 | — | 19.0 | 31.2 | 3.1 | 26.7 |

All IgG anti-lymphoma MAbs showed some ADCC activity with the different canine blood cell populations. For the same donor the ADCC values by PBL were usually higher than those presented by the nonadherent lymphocytes. Adherent monocyte enriched fractions gave consistently higher values than those presented by PBL or lymphocytes. In every case MAb 234-2a presented the highest ADCC values. MAb 231 and 254 showed significant ADCC activity with monocyte effectors. MAbs 212 and 234 were less effective in killing the target cell in combination with monocytes. MAb 231 presented a little higher ADCC activity with canine PBL than any other of the MAbs except 234-2a MAb. MAbs 234 and 234-2a with canine lymphocyte effector cells gave similar ADCC values, both a little higher than those of the other anti-lymphoma MAbs: 212, 231, and 254. Anti-lymphoma MAbs of the IgG$_{2a}$ subclass (231 and 234-2a) and IgG$_3$ (254) presented the highest ADCC values on canine target lymphoma 17-71 cells. MAbs 212 and 234 both of the IgG$_1$ subclass were less effective in mediating ADCC (Table 7).

The invention now being fully described, it will be apparent to one of ordinary skill in that art that many changes and modification can be made without departing from the spirit or scope of the invention.

We claim:

1. A continuous hybridoma cell line which secretes monoclonal antibodies which are at least twice as reactive with canine lymphoma cells as with normal canine lymphocytes as determined by the percentage of positive cells by FACS (fluorescence activated cell sorting), and which do not react with DR-related antigens (i.e. differentiation or transplantation antigens similar to HLA-DR in man and Ia in mouse).

2. The hybridoma of claim 1, wherein said hybridoma is selected from the group consisting of ATCC HB 9401, ATCC HB 9402 and ATCC HB 9403 and their isotype switch variants.

3. A monoclonal antibody which is at least twice as reactive with canine lymphoma cells as with normal canine lymphocytes as determined by the percentage of positive cells by FACS (fluorescence activated cell sorting), and which does not react with DR-related antigens.

4. The monoclonal antibody, according to claim 3, wherein said monoclonal antibody is produced by a hybridoma cell line selected from the group consisting of ATCC HB 9401, ATCC HB 9402, and ATCC HB 9403.

5. The monoclonal antibody, according to claim 3, having the specificity of a monoclonal antibody produced by a hybridoma cell line selected from the group consisting of ATCC HB 9401, ATCC HB 9402 and ATCC HB 9403.

6. A chimeric antibody comprising the $V_L$ and $V_H$ domains of a monoclonal antibody, according to claim 3.

7. The chimeric antibody of claim 6, wherein said monoclonal antibody is produced by a cell line selected from the group consisting of ATCC HB 9401, ATCC HB 9402 and ATCC HB 9403.

8. The cell line of claim 1 wherein said monoclonal antibodies have the antigenic specificity of a monoclonal antibody produced by a hybridoma selected from the group consisting of ATCC HB 9401, ATCC HB 9402, and ATCC HB 9403.

9. The chimeric antibody of claim 6 wherein said monoclonal antibody has the antigenic specificity of a monoclonal antibody produced by a hybridoma selected from the group consisting of ATCC HB 9401, ATCC HB 9402, and ATCC HB 9403.

10. A veterinary composition comprising lymphomatous disease suppressing amounts of a monoclonal antibody, wherein said antibody has the antigenic specificity of a monoclonal antibody produced by ATCC HB 9401, ATCC HB 9402 or ATCC HB 9403 together with a pharmaceutically inert carrier.

* * * * *